United States Patent [19]

Akiba et al.

[11] 4,402,734
[45] Sep. 6, 1983

[54] HERBICIDIAL COMPOSITION AND METHOD

[75] Inventors: Keiichiro Akiba, Ikeda; Takeo Satomi, Amagasaki; Akira Fujinami, Ashiya; Yasuhisa Asano, Minoo; Nobuyuki Kameda, Takarazuka; Akihiko Mine; Naganori Hino, both of Toyonaka; Kohshi Tateishi, Minoo, all of Japan

[73] Assignee: Sumitomo Chemical Co., Ltd., Osaka, Japan

[21] Appl. No.: 407,359

[22] Filed: Oct. 17, 1973

Related U.S. Application Data

[62] Division of Ser. No. 235,044, Mar. 15, 1972, Pat. No. 3,780,090.

[30] Foreign Application Priority Data

Mar. 15, 1971 [JP] Japan .................. 46-14609

[51] Int. Cl.³ ............................................ A01N 37/46
[52] U.S. Cl. ........................................ 71/111; 71/115; 560/43; 562/456
[58] Field of Search .................. 71/111, 118, 115; 260/471 A

[56] References Cited

U.S. PATENT DOCUMENTS

| | | | |
|---|---|---|---|
| 3,403,994 | 10/1968 | Olin | 71/118 |
| 3,439,018 | 4/1969 | Brookes et al. | 71/118 |
| 3,442,945 | 5/1969 | Olin | 71/118 |
| 3,539,618 | 11/1970 | Stoffel | 71/111 |
| 3,598,859 | 8/1971 | Yates et al. | 71/111 |
| 3,780,095 | 12/1973 | Klemm et al. | 260/471 A |
| 3,830,829 | 8/1974 | Olin | 71/111 |

*Primary Examiner*—Richard Raymond
*Attorney, Agent, or Firm*—Sughrue, Mion, Zinn, Macpeak and Seas

[57] ABSTRACT

A herbicidal composition comprising a herbicidally effective amount of N-halogenoacylanilino-fatty acid or the ester derivative thereof represented by the general formula:

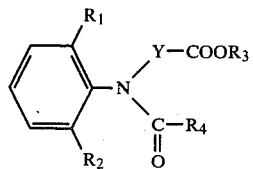

wherein $R_1$ and $R_2$ each represents $C_1$–$C_4$ allyl, $R_3$ represents a hydrogen atom, alkyl having up to 10 carbon atoms, $C_3$–$C_5$ alkenyl, $C_3$–$C_4$ alkynyl or cyclohexyl, $R_4$ represents lower alkyl substituted by 1–4 halogen atoms and Y represents $C_1$–$C_3$ alkylene, as an effective ingredient, and a herbicidally effective inert carrier.

11 Claims, No Drawings

HERBICIDIAL COMPOSITION AND METHOD

This is a division of application Ser. No. 235,044, filed Mar. 15, 1972, now U.S. Pat. No. 3,780,090, issued Dec. 18, 1973.

This invention relates to novel N-halogenoacylaniline-fatty acid or the ester derivative thereof as an effective ingredient, to a process for producing the same and to herbicidal composition containing the same.

More particularly, the present invention relates to (1) a novel N-halogenoacylanilino-fatty acid or the ester derivative thereof represented by the general formula(I);

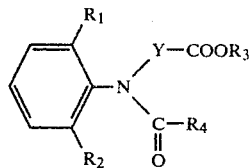

wherein $R_1$ and $R_2$ each represents lower $C_1$–$C_4$ alkyl group, $R_3$ represents hydrogen atom, alkyl, lower $C_3$–$C_5$ alkenyl group or lower $C_3$–$C_4$ alkynyl group, $R_4$ represents lower alkyl group substituted by 1–4 halogen atom, and Y represents lower $C_1$–$C_3$ alkylene group, (2) a process for preparing the compound of the formula(I), which comprises reacting anilino-fatty acid or the ester derivative thereof represented by the general formula (II);

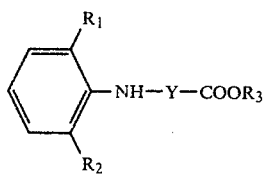

wherein $R_1$, $R_2$, $R_3$ and Y are the same as defined above, with halogeno-fatty acid halide represented by the general formula (III);

$$R_4COX \qquad (III)$$

wherein $R_4$ is the same as defined above and X is a halogen atom, in the presence of a suitable dehydrohalogenating agent to obtain N-halogenoacylanilino-fatty acid or the ester derivative thereof represented by the general formula (I), and (3) a process for preparing the compound of the formula (I) which comprises reacting alkali metal salt of halogeno-fatty acid anilide derivative represented by the general formula (IV);

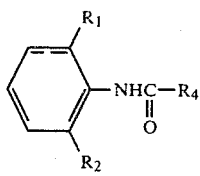

wherein $R_1$, $R_2$ and $R_4$ are the same as defined above, with halogeno-fatty acid ester represented by the general formula (V);

$$Z-Y-COOR_3 \qquad (V)$$

wherein Y and $R_3$ are the same as defined above, and Z represents halogen atom, or with the ester derivative thereof to obtain N-halogenoacylanilino-fatty acid represented by the general formula (I) or the ester derivative thereof and to (4) herbicidal composition containing the compound of the formula (I) as an effective ingredient.

N-halogenoacylanilino-fatty acid and the ester derivative thereof obtained by the present invention are novel, and it has found by present inventors that they possess strong herbicidal activity which could not be expected from other analogous publicly known compounds, and extremely advantageous selectivity.

That is, the compounds of the present invention have a strong weed-killing effect to a wide scope of weeds and, for example, they have an excellent weed-killing effect to both grassy weeds such as barnyardgrass (*Echinochloa crusgalli*), large crabgrass (*Digitaria sanguinalis*), water foxtail (*Alopecurus aequalis*), annual bluegrass (*Poa annua*), etc. and broad-leaf weeds such as chick weed (*Stellaria media*), common purslane (*Portulaca oleracea*), redroot pigweed (*Amaranthus retroflexus*), monochoria (*Monochoria vaginalis*), false pimpernel (*Linderna pyxidaria*), etc. Furthermore, the compounds of the present invention are characterized in that they have selectivity toward various crops, and thus, they are capable of controlling weeds without causing any phytotoxicity, for example, to radish, cabbage, pea, sugar beet, burdock, tomato, cotton, wheat, corn, etc.

In addition, the use thereof in a paddy field is extremely effective due to the greatly strong weed-killing effect thereof, and the compounds are capable of controlling main weeds growing in a paddy field, such as barnyardgrass, monochoria, false pimpernel, (*Rotala indica*), nutsedge sp. (*Cyperus difformis*), etc. without causing any phytotoxicity to transplanted rice and, furthermore, the compounds have excellent effect of controlling even a perennial plant, slender spikerush which is difficult to control.

The compounds of the present invention are useful as a herbicide for various cereals such as rice, corn, etc., vegetables, fruit trees, a lawn, a meadow, forest, non-farming land, etc.

The present invention (1) has been completed on the basis of the above-mentioned novel knowledge, and relates to a novel N-halogenoacetylanilino-fatty acid or the ester derivative thereof represented by the general formula (I) and to their herbicidal composition.

The invention (2) and (3) relates to a process for producing the same and, in the invention (2), N-halogenoacylanilino-fatty acid or the ester derivative thereof can be obtained in general by dissolving anilino-fatty acid or the ester derivative thereof represented by the general formula (II) and equimolar amount of halogeno-fatty acid halide represented by the general formula (III) in an inert solvent such as benzene, toluene, xylene, ethyl ether, isopropyl ether, ligroin, hexane, acetone, methyl isobutyl ketone, chloroform or carbon tetrachloride, preferably, in benzene, adding dropwise equivalent amount of dehydrohalogenating agent such as pyridine, triethylamine, N,N-diethylaniline, N-methyl-morpholine, sodium carbonate or potassium carbonate, preferably, triethylamine, stirring the mixture for a while, then washing the resulting solution with successive, dilute hydrochloric acid, dilute alkali aqueous solution, and water, and, after drying, removing the solvent to obtain the pure end product in good yield.

In the invention (3), N-halogenoacylanilino-fatty acid or the ester derivative thereof can be obtained by dissolving halogeno-fatty acid anilide derivative in an appropriate solvent such as diethyl ether, isopropyl ether, tetrahydrofuran, dioxane, benzene, toluene or xylene, preferably, in tetrahydrofuran, adding equivalent amount of alkali metal such as sodium, potassium, lithium, etc., or alkyl alkali or phenyl alkali derivative to form alkali metal salt of halogeno-fatty acid anilide derivative, adding thereto equimolar amount of halogeno-fatty acid represented by the general formular (V) or the ester derivative thereof, stirring the mixture, if necessary, under heating and, after the completion of reaction, removing the solvent and inorganic salts to obtain pure end product in good yield.

Examples of each of the starting materials employed in the present invention are illustrated below but of course the present invention is not limited by them.

Anilino fatty acid and the ester derivative thereof:
2,6-dimethylanilino-acetic acid;
methyl 2-6-dimethylanilino-acetate;
ethyl 2,6-dimethylanilino-acetate;
n-propyl 2,6-dimethylanilino-acetate;
iso-propyl 2,6-dimethylanilino-acetate;
n-butyl 2,6-dimethylanilino-acetate;
iso-butyl 2,6-dimethylanilino-acetate;
2-methyl-6-ethylanilino-acetic acid;
methyl 2-methyl-6-ethylanilino-acetate;
ethyl 2-methyl-6-ethylanilino-acetate;
n-propyl 2-methyl-6-ethylanilino-acetate;
2,6-diethylanilino-acetic acid;
methyl 2,6-diethylanilino-acetate;
ethyl 2,6-diethylanilino-acetate;
n-propyl 2,6-diethylanilino-acetate;
2,6-di-n-propylanilino-acetic acid;
methyl 2,6-di-n-propylanilino-acetate;
ethyl 2,6-di-n-propylanilino-acetate;
n-propyl 2,6-di-n-propylanilino-acetate;
n-butyl 2,6-di-n-propylanilino-acetate;
methyl α-(2,6-dietylanilino)propionate;
ethyl α-(2,6-diethylanilino)propionate;
n-propyl α-(2,6-diethylanilino)propionate;
methyl β-(2,6-diethylanilino)propionate;
ethyl β-(2,6-diethylanilino)propionate;
n-propyl β-(2,6-diethylanilino)propionate;
methyl α-(2,6-dimethylanilino)propionate;
ethyl α-(2,6-dimethylanilino)propionate;
n-propyl α-(2,6-dimethylanilino)propionate;
α-(2-methyl-6-ethylanilino)propionic acid;
methyl α-(2-methyl-6-ethylanilino)propionate;
ethyl α-(2-methyl-6-ethylanilino)propionate;
n-propyl-α-(2-methyl-6-ethylanilino)propionate;
n-amyl 2,6-dimethylanilino-acetate;
n-hexyl 2,6-dimethylanilino-acetate;
cyclohexyl 2,6-dimethylanilino-acetate;
n-dexyl 2,6-dimethylanilino-acetate;
iso-amyl 2,6-dimethylanilino-acetate;
allyl 2,6-dimethylanilino-acetate;
crotonyl 2,6-dimethylanilino-acetate;
β-methylallyl 2,6-dimethylanilino-acetate;
n-amyl-2-methyl-6-ethylanilino-acetate;
cyclohexyl 2-methyl-6-ethylanilino-acetate;
allyl 2-methyl-6-ethylanilino-acetate;
crotonyl 2-methyl-6-ethylanilino-acetate;
n-amyl-2,6-diethylanilino-acetate;
sec-amyl 2,6-diethylanilino-acetate;
crotonyl 2,6-diethylanilino-acetate;
β-methallyl 2,6-diethylanilino-acetate;
n-decyl 2,6-diethylanilino-acetate;
cyclohexyl 2,6-diethylanilino-acetate;
n-amyl α-2,6-dimethylanilino-propionate;
cyclohexyl α2,6-dimethylanilino-propionate;
allyl α2,6-dimethylanilino-propionate;
n-amyl α2,6-diethylanilino-propionate;
n-hexyl α2,6-diethylanilino-propionate;
n-heptyl α2,6-diethylanilino-propionate;
allyl α2,6-diethylanilino-propionate;
crotonyl α2,6-diethylanilino-propionate;
propargyl 2,6-diethylanilino-acetate;

Halogeno-fatty acid halide:
monochloroacetic acid chloride;
monobromoacetic acid chloride;
monoiodoacetic acid chloride;
monofluoroacetic acid chloride;
monochloroacetic acid bromide;
monobromoacetic acid bromide;
monoiodoacetic acid bromide;
monofluoroacetic acid bromide;
dichloroacetic acid chloride;
dibromoacetic acid chloride;
trichloroacetic acid chloride;
trifluoroacetic acid chloride;
α,α-dichloropropionic acid chloride;
α,β,β-tetrafluoropropionic acid chloride, Halogeno-fatty acid anilide;
2,6-dimethyl-monochloroacetic acid anilide;
2,6-dimethyl-monobromoacetic acid anilide;
2,6-dimethyl-monoiodoacetic acid anilide;
2,6-dimethyl-monofluoroacetic acid anilide;
2,6-dimethyl-dichloroacetic acid anilede;
2,6-dimethyl-trichloroacetic acid anilide;
2,6-dimethyl-trifluoroacetic acid anilide;
2,6-dimethyl-α,α-dichloropropionic acid anilide;
2-methyl-6-ethyl-monochloroacetic acid anilide;
2-methyl-6-ethyl-monobromoacetic acid anilide;
2-methyl-6-ethyl-monoiodoacetic acid anilide;
2-methyl-6-ethyl-monofluoroacetic acid anilide;
2-methyl-6-ethyl-trichloroacetic acid anilide;
2-methyl-6-ethyl-α,α,β,β-tetrafluoropropionic acid anilide;
2,6-diethyl-monochloroacetic acid anilide;
2,6-diethyl-monobromoacetic acid anilide;
2,6-diethyl-monoiodoacetic acid anilide;
2,6-diethyl-monofluoroacetic acid anilide;
2,6-diethyl-trichloroacetic acid anilide;
2,6-diethyl-trifluoroacetic acid anilide;
2,6-diethyl-α,α-dichloropropionic acid anilide;
2,6-diethyl-α,α,β,β-tetrafluoropropionic acid anilide;
2,6-di-n-propyl-monochloroacetic acid anilide;
2,6-di-n-propyl-monobromoacetic acid anilide;
2,6-di-n-propyl-monoiodoacetic acid anilide;
2,6-di-n-propyl-monofluoroacetic acid anilide;
2,6-di-n-propyl-trichloroacetic acid anilide;
2,6-di-n-propyl-α,α-dichloropropionic acid anilide;
2,6-di-n-propyl-dichloroacetic acid anilide;
2,6-di-n-propyl-trifluoroacetic acid anilide;

Halogeno-fatty acid and the ester derivative thereof.
monochloroacetic acid;
methyl monochloroacetate;
ethyl monochloroacetate;
n-propyl monochloroacetate;
iso-propyl monochloroacetate;

n-butyl monochloroacetate;
iso-butyl monochloroacetate;
monobromoacetic acid;
methyl monobromoacetate;
ethyl monobromoacetate;
n-propyl monobromoacetate;
n-butyl monobromoacetate;
propargyl monobromoacetate;
monoiodoacetic acid;
methyl monoiodoacetate;
ethyl monoiodoacetate;
n-propyl monoiodoacetate;
n-butyl monoiodoacetate;
dichloroacetic acid;
methyl dichloroacetate;
ethyl dichloroacetate;
n-propyl dichloroacetate;
trichloroacetic acid;
methyl trichloroacetate;
ethyl trichloroacetate;
n-butyl trichloroacetate;
α,α-dichloropropionic acid;
methyl α,α-dichloropropionate;
ethyl α,α-dichloropropionate;
α,α-β,β-tetrafluoropropionic acid;
methyl α,α-β,β-tetrafluoropropionate;
ethyl α,α-β,β-tetrafluoropropionate;
n-propyl α,α,β,β-tetrafluoropropionate;

In a practical application, the compounds of the present invention may be spread as such, or may be used in any form of granule, wettable powder, emulsion, and dust.

As the solid carriers used in preparing these preparations, there are illustrated, for example, talc, bentonite, clay, kaolin, diatomaceous earth, vermiculite, slaked lime, etc. and, as the liquid carriers, there are illustrated benzene, toluene, xylene, alcohols, acetone, methylnaphthalene, diozane, cyclohexanone, etc. As the emulsifying agents, there are illustrated alkylsulfuric esters, alkylsulfonate, arylsulfonate, polyethylene glycol ethers, polyhydric alcohol esters, etc.

In a practical application, a speader such as a surface active agent used in agricultural field may of course be mixed so as to improve and ensure the herbicidal effect, and, it is also possible to use in combination with other agricultural chemicals such as fungicides, insecticides, herbicides, etc., or with fertilizers.

The combination examples of the composition of the present invention are shown below.

EXAMPLE 1

25 Parts by weight of N-chloroacetyl-2,6-diethylanilinoacetic acid, 5 parts by weight of polyoxyethylene acetylaryl ester surface active agent and 70 parts by weight of talc are well crushed and mixed to obtain a wettable powder.

EXAMPLE 2

25 Parts by weight of N-chloroacetyl-2,6-dimethylanilinoacetic acid n-amyl ester, 5 parts by weight of polyoxyethylene acetylaryl ester surface active agent and 70 parts by weight of talc are well crushed and mixed to obtain a wettable powder.

EXAMPLE 3

30 Parts by weight of ethyl N-chloroacetyl-2,6-diethylanilinoacetate, 20 parts by weight of polyethylene glycol ether surface active agent and 50 parts by weight of cyclohexanone are well mixed to obtain an emulsion.

EXAMPLE 4

30 Parts by weight of n-decyl N-chloroacetyl-2,6-diethylanilino-acetate, 20 parts by weight of polyethylene glycol ether surface active agent and 50 parts by weight of cyclohexanone are well mixed to obtain an emulsion.

EXAMPLE 5

8 Parts by weight of ethyl N-chloroacetyl-2,6-diethylanilinoacetate, 38 parts by weight of bentonite, 50 parts by weight of clay and 4 parts by weight of sodium lignin sulfonate are well crushed and mixed, and, after well kneading with the addition of water, granulated and dried to obtain a granule.

EXAMPLE 6

8 Parts by weight of allyl N-dichloroacetyl-2,6-diethylanilinoacetate, 38 parts by weight of bentonite, 50 parts by weight of clay and 4 parts by weight of sodium lignin sulfonate are well crushed and mixed, and, after kneading with the addition of water, granulated and dried to obtain a granule.

The present invention will be explained in greater detail by the following Examples, but not limited only to them as a matter of course.

EXAMPLE 7

23.5 Grams (0.1 mol) of ethyl 2,6-diethylanilinoacetate and 11.3 g (0.1 mol) of monochloroacetic acid chloride were dissolved in 100 ml of benzene, 11.0 g of triethylamine was then added dropwise thereto with stirring maintaining the reaction temperature at 10°–20° C. and, thereafter, stirring was continued for further 2 hours at a room temperature. The reaction solution was washed with successive, 5% sodium hydroxide aqueous solution, 5% hydrochloric acid aqueous solution, and water. Then, the benzene layer was dried over anhydrous sodium sulfate. Thereafter, benzene was removed under reduced pressure to obtain the end product, ethyl N-chloroacetyl-2,6-diethylanilinoacetate. $n_D^{26}$: 1.5225.

| Elementary analysis: | | | | |
|---|---|---|---|---|
| | C (%) | H (%) | N (%) | Cl (%) |
| Calculated for $C_{16}H_{22}NClO_3$ | 61.63 | 7.11 | 4.49 | 11.37 |
| Found: | 61.81 | 7.08 | 4.42 | 11.48 |

The results obtained in the similar manner as above shown in the following Table 1.

TABLE 1

| Ex. No. | Anilino-fatty acid or the ester thereof | Halogeno-acetic acid halide | N—halogenoacylanilino-fatty acid or the ester derivative thereof | | | | | | |
|---|---|---|---|---|---|---|---|---|---|
| | | | Chemical structure | Physical constant | Yield (%) | Elementary analysis | | | |
| | | | | | | C (%) | H (%) | N (%) | Cl (%) |
| 8 | Ethyl 2,6-dimethyl-anilino-acetate | ClCH$_2$COCl | [structure: 2,6-dimethylphenyl-N(CH$_2$COOC$_2$H$_5$)(COCH$_2$Cl)] | $n_D^{23}$ 1.3647 bp$_{0.4}$ 136–138° C. | 85 | Calcd.: 59.26 Found: 59.37 | 6.39 6.28 | 4.94 5.02 | 12.50 12.51 |
| 9 | Ethyl 2-methyl-6-ethyl-anilino-acetate | ClCH$_2$COCl | [structure: 2-methyl-6-ethylphenyl-N(CH$_2$COOC$_2$H$_5$)(COCH$_2$Cl)] | $n_D^{22}$ 1.5271 bp$_{0.7}$ 161–163° C. | 88 | Calcd.: 60.50 Found: 60.47 | 6.77 6.85 | 4.70 4.66 | 16.12 16.23 |
| 10 | Ethyl 2,6-dimethyl-anilino-acetate | Cl$_3$CCOCl | [structure: 2,6-dimethylphenyl-N(CH$_2$COOC$_2$H$_5$)(COCCl$_3$)] | $n_D^{21.5}$ 1.4230 bp$_{0.6}$ 162–163° C. | 75 | Calcd.: 47.68 Found: 47.54 | 4.57 4.54 | 3.97 3.87 | 30.16 30.20 |

EXAMPLE 11

22.6 Grams (0.1 mol) of 2.6-diethyl-chloroacetonailide was dissolved in 100 ml of tetrahydrofuran, and 45 g of n-hexane solution containing 15% of n-butyl lithium was gradually added dropwise thereto at a room temperature with stirring. Furthermore, 12.3 g (0.1 mol) of ethyl monochloroacetate was added thereto, and the mixture was refluxed for 4 hours. After cooling, 20 g of ethanol was added to the reaction mixture, and the solvent was removed under reduced pressure. The resulting residue was extracted with 100 ml of diethyl ether. After washing with water, the ether layer was dried over anhydrous sodium sulfate, and the solvent was removed to obtain 24.9 g of the end product, ethyl N-chloroacetyl-2,6-diethylanilinoacetate. $n_D^{24}$: 1.5228.

| | Elementary analysis: | | | |
|---|---|---|---|---|
| | C (%) | H (%) | N (%) | Cl (%) |
| Calcd. for C$_{16}$H$_{22}$NClO$_3$: | 61.63 | 7.11 | 4.49 | 11.37 |
| Found: | 61.77 | 7.20 | 4.46 | 11.22 |

The results obtained in the similar manner as above are shown in the following Table 2.

TABLE 2

| Ex. No. | Mono-halogeno-acetic acid amide | Halogeno-fatty acid or the ester thereof | N—halogenoacylanilino-fatty acid or the ester derivative thereof obtained | | | | | | |
|---|---|---|---|---|---|---|---|---|---|
| | | | Chemical structure | Physical constant | Yield (%) | Elementary analysis | | | |
| | | | | | | C (%) | H (%) | N (%) | Cl (%) |
| 11 | N—(2,6-dimethyl-phenyl) monochloro-acetamide | Ethyl mono-chloro-acetate | [structure: 2,6-dimethylphenyl-N(CH$_2$COOC$_2$H$_5$)(COCH$_2$Cl)] | $n_D^{23}$ 1.3645 bp$_{0.35}$ 134–137° C. | 78 | Calcd.: 59.26 Found: 59.41 | 6.39 6.49 | 4.94 4.81 | 12.50 12.57 |
| 12 | N—(2-methyl-6-ethyl-phenyl)-monochloro-acetamide | Ethyl mono-bromo-acetate | [structure: 2-methyl-6-ethylphenyl-N(CH$_2$COOC$_2$H$_5$)(COCH$_2$Cl)] | $n_D^{22}$ 1.5274 bp$_{0.7}$ 160–164° C. | 69 | Calcd.: 60.50 Found: 60.54 | 6.77 6.69 | 4.70 4.83 | 16.12 16.14 |

TABLE 2-continued

| Ex. No. | Mono-halogeno-acetic acid amide | Halogeno-fatty acid or the ester thereof | N—halogenoacylanilino-fatty acid or the ester derivative thereof obtained | | | | | | |
|---|---|---|---|---|---|---|---|---|---|
| | | | Chemical structure | Physical constant | Yield (%) | Elementary analysis | | | |
| | | | | | | C (%) | H (%) | N (%) | Cl (%) |
| 13 | N—(2,6-diethylphenyl) monochloroacetamide | Butyl monochloroacetate | (structure with $C_2H_5$ groups, $CH_2COOC_4H_9$, $CCH_2Cl$, O) | $n_D^{23.5}$ 1.5176 | 86 | Calcd.: 63.21 Found: 63.59 | 7.71 7.82 | 4.12 4.29 | 10.43 10.37 |

EXAMPLE 14

24.7 Grams of allyl 2,6-diethylanilinoacetate and 11.3 g of monochloroacetic acid chloride were dissolved in 100 ml of benzene, 11.0 g of triethylamine was then added dropwise thereto with stirring maintaining the reaction temperature at 10°–20° C., and, thereafter, stirring was continued for further 2 hours at a room temperature. The reaction solution was washed with successive, 5% sodium hydroxide aqueous solution, 5% hydrochloric acid aqueous solution, and water. Then, the benzene layer was dried over anhydrous sodium sulfate. Thereafter, benzene was removed under reduced pressure to obtain the end product, allyl N-chloroacetyl-2,6-diethylanilinoacetate. $n_D^{21.5}$: 1.5288.

| Elementary analysis: | | | | |
|---|---|---|---|---|
| | C (%) | H (%) | N (%) | Cl (%) |
| Calcd. for $C_{17}H_{22}NClO_3$: | 63.05 | 6.85 | 4.33 | 10.95 |
| Found: | 63.09 | 6.85 | 4.19 | 10.88 |

The results obtained in the similar manner as above are shown in the following Table 3.

TABLE 3

N—halogenoacylanilino-fatty acid ester obtained

| Example No. | Anilino-fatty acid ester used | Halogeno-fatty acid halide used | Chemical structure | Physical constant | Yield (%) | | C (%) | H (%) | N (%) | Cl (%) |
|---|---|---|---|---|---|---|---|---|---|---|
| 15 | 2,6-dimethylanilino with NHCH$_2$COOC$_5$H$_{11}$(n) | ClCH$_2$COCl | N-acyl derivative with CH$_2$COOC$_5$H$_{11}$(n) and CCH$_2$Cl/O | $n_D^{24}$ 1.5263 | 86 | Calcd.: Found: | 62.67 62.54 | 7.42 7.58 | 4.30 4.20 | 10.88 10.81 |
| 16 | 2,6-diethylanilino with NHCH$_2$COOC$_{10}$H$_{21}$(n) | ClCH$_2$COBr | N-acyl derivative with CH$_2$COOC$_{10}$H$_{21}$(n) and CCH$_2$Cl/O | $n_D^{23}$ 1.5297 | 71 | Calcd.: Found: | 67.98 68.05 | 9.03 8.99 | 3.30 3.34 | 8.36 8.16 |
| 17 | 2,6-diethylanilino with NHCH$_2$COOCH$_2$CH=CH$_2$ | Cl$_2$CHCOCl | N-acyl derivative with CH$_2$COOCH$_2$CH=CH$_2$ and C—CHCl$_2$/O | $n_D^{23}$ 1.5376 | 82 | Calcd.: Found: | 56.99 57.18 | 5.91 5.77 | 3.91 3.90 | 19.79 19.75 |
| 18 | 2-methyl-6-propylanilino with NHCH$_2$COOCH$_2$C(CH$_3$)=CH$_2$ | BrCH$_2$COCl | N-acyl derivative with CH$_2$COOCH$_2$C(CH$_3$)=CH$_2$ and C—CH$_2$Br/O | $n_D^{22}$ 1.5325 | 77 | Calcd.: Found: | 56.55 56.72 | 6.33 6.30 | 3.66 3.87 | 20.90 21.11 |
| 19 | 2,6-diethylanilino with NHCH$_2$COO-cyclohexyl | Cl$_3$COCl | N-acyl derivative with CH$_2$COO-cyclohexyl and CCl$_3$/O | $n_D^{23}$ 1.5441 | 65 | Calcd.: Found: | 55.25 55.34 | 6.03 6.16 | 3.22 3.24 | (Bromine) 24.46 24.53 |

TABLE 3-continued

| Example No. | Anilino-fatty acid ester used | Halogeno-fatty acid halide used | N—halogenoacylanilino-fatty acid ester obtained | | | | Elementary analysis | | |
| --- | --- | --- | --- | --- | --- | --- | --- | --- | --- |
| | | | Chemical structure | Physical constant | Yield (%) | | C (%) | H (%) | N (%) | Cl (%) |
| 20 | 2,6-diethyl-C₆H₃-NHCH₂COOCH₂C≡CH | ClCH₂COCl | 2,6-diethyl-C₆H₃-N(CH₂COOCH₂C≡CH)(COCH₂Cl) | $n_D^{22.5}$ 1.5408 | 84 | Calcd.: 63.45 | 6.26 | 4.35 | 11.02 |
| | | | | | | Found: 63.52 | 6.48 | 4.17 | 10.94 |

TEST EXAMPLE 1

Barnyard grass and large crabgrass as the representative of grassy weeds, and radish and red root pigweed as the representative of broad-leaf plants each was sown in an unglazed flower pot of 12 cm in diameter, and, after covering with the soil, treated with the chemicals. Thereafter, these plants were reared in a greenhouse, and the herbicidal effect was observed 20 days after the treatment. The results are shown in Table 4. The estimation of the herbicidal effect is expressed by numerals of from 0 (no injuries) to 5 (completely dead). All the compounds were used in the form of wettable powder diluted with water.

TABLE 4

| Compound | Applied amount (g/10a) | Barnyard grass | large crabgrass | red root pigweed | Radish |
|---|---|---|---|---|---|
| N—chloroacetyl-2,6-diethyl-anilinoacetic acid ethyl ester | 125 | 5 | 5 | 5 | 0 |
| | 63 | 5 | 5 | 4 | 0 |
| | 32 | 5 | 5 | 2 | 0 |
| | 16 | 5 | 4 | 1 | 0 |
| Ethyl N—chloroacetyl-2-methyl-6-n-propyl-anilinoacetate | 125 | 5 | 5 | 5 | 0 |
| | 63 | 5 | 5 | 3 | 0 |
| | 32 | 5 | 5 | 1 | 0 |
| 2-chloro-2',6'-diethylacetoanilide* | 125 | 5 | 4 | 2 | 0 |
| | 63 | 4 | 4 | 0 | 0 |
| | 32 | 1 | 1 | 0 | 0 |
| n-Amyl N—chloroacetyl-2,6-dimethylanilinoacetate | 125 | 5 | 5 | 5 | 0 |
| | 63 | 5 | 5 | 3 | 0 |
| | 32 | 4 | 5 | 1 | 0 |
| Allyl N—dichloroacetyl-2,6-diethyl-anilinoacetate | 125 | 5 | 5 | 5 | 0 |
| | 63 | 5 | 5 | 4 | 0 |
| | 32 | 5 | 5 | 2 | 0 |
| 2-Chloro-2',6'-diethylacetoanilide* | 125 | 5 | 4 | 2 | 0 |
| | 63 | 4 | 4 | 0 | 0 |
| | 32 | 1 | 1 | 0 | 0 |

*Control Compound

TEST EXAMPLE 2

1.5 Kg of paddy field soil was placed in each of Wagner pot of 14 cm in diameter, and the pots were brought into a paddy field state. Thereafter, third-leaf period rice seedlings were transplanted to the pot, which was further sown with the seeds of barnyard grass, and the water-flooded soil was treated with prescribed amount of the chemicals. On the 25th day after the treatment with the chemicals, the herbicidal effect and the degree of phytotoxicity were investigated about the transplanted or sown plants described above, and the spontaneously generated broad-leaf weeds such as monochoria, false pimpernel, Rotala indica Koehne, etc. and slender spikerush. The chemicals were applied in the form of an emulsion prepared according to the same prescription as in the Example 2 described above. The results are shown in Table 5. The estimations of herbicidal effect and phytotoxicity were expressed by numerals of 0–5 as follows.

| 0 | Action on plants | Nothing |
|---|---|---|
| 1 | Action on plants | Slight |
| 2 | Action on plants | Small |
| 3 | Action on plants | Middle |
| 4 | Action on plants | Large |
| 5 | Action on plants | Completely dead |

TABLE 5

Water-flooded soil treatment test.

| Compound | Applied amount (g/10a) | Phytotoxicity to rice | Herbicidal effect Barnyard grass | Herbicidal effect Broad-leaf weeds | Herbicidal effect Slender spikerush |
|---|---|---|---|---|---|
| Ethyl N—chloroacetyl-2,6-diethyl-anilinoacetate | 63 | 0 | 5 | 5 | 3 |
| | 32 | 0 | 5 | 5 | 2 |
| | 16 | 0 | 5 | 4 | 0 |
| | 8 | 0 | 5 | 2 | 0 |
| Ethyl N—chloroacetyl-2-methyl-6-n-propyl-anilinoacetate | 63 | 0 | 5 | 5 | 3 |
| | 32 | 0 | 5 | 5 | 2 |
| | 16 | 0 | 5 | 3 | 0 |
| Butyl N—chloroacetyl-2,6-diethyl-anilinoacetate | 63 | 0 | 5 | 5 | 4 |
| | 32 | 0 | 5 | 5 | 3 |
| | 16 | 0 | 5 | 4 | 0 |
| 2-Chloro-2,6-diethyl-acetanilide* | 63 | 0 | 5 | 3 | 0 |
| | 32 | 0 | 4 | 0 | 0 |
| | 16 | 0 | 2 | 0 | 0 |
| n-Amyl N—chloroacetyl-2,6-dimethyl-anilino-acetate | 63 | 0 | 5 | 5 | 3 |
| | 32 | 0 | 5 | 5 | 2 |
| | 16 | 0 | 5 | 3 | 0 |
| Allyl N—dichloroacetyl-2,6-diethyl-anilino-acetate | 63 | 0 | 5 | 5 | 3 |
| | 32 | 0 | 5 | 5 | 3 |
| | 16 | 0 | 5 | 4 | 1 |
| 2-Chloro-2',6'-diethylacetanilide* | 63 | 0 | 5 | 3 | 0 |
| | 32 | 0 | 4 | 0 | 0 |
| | 16 | 0 | 2 | 0 | 0 |

*Control compound

What is claimed is:

1. A herbicidal composition comprising a herbicidally effective amount of N-halogenoacylanolino-fatty acid or the ester derivative thereof represented by the general formula:

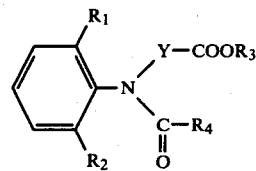

wherein $R_1$ and $R_2$ each represents $C_1$–$C_4$ alkyl, $R_3$ represents a hydrogen atom, alkyl having up to 10 carbon atoms, $C_3$–$C_4$ alkenyl, propargyl or cyclohexyl, $R_4$ represents $C_1$–$C_3$ alkyl substituted by 1–4 halogen atoms and Y represents $C_1$–$C_3$ alkylene, as an effective ingredient, and a herbicidally acceptable inert carrier.

2. The herbicidal composition according to claim 1, wherein said effective ingredient is the compound of the formula:

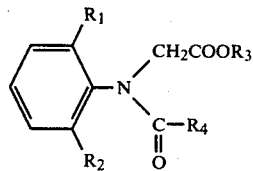

wherein $R_1$, $R_2$, $R_3$ and $R_4$ are the same as defined in claim 1.

3. The herbicidal composition according to claim 1, wherein said effective ingredient is the compound of the formula:

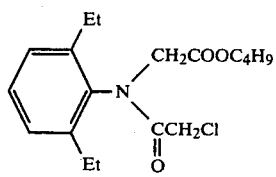

4. The herbicidal composition according to claim 1, wherein said effective ingredient is the compound of the formula:

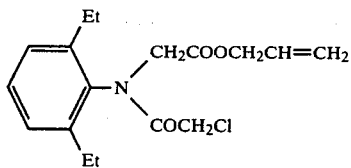

5. The herbicidal composition according to claim 1, wherein said effective ingredient is the compound of the formula:

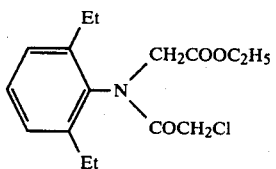

6. A method of controlling weeds which comprises applying an effective amount of a composition containing N-halogenoacylanilino-fatty acid or the ester derivative thereof of the formula:

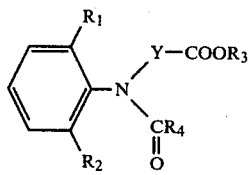

wherein $R_1$ and $R_2$ each represents $C_1$-$C_4$ alkyl, $R_3$ represents a hydrogen atom, alkyl having up to 10 carbon atoms, $C_3$-$C_4$ alkenyl, propargyl or cyclohexyl, $R_4$ represents $C_1$-$C_3$ alkyl substituded by 1 to 4 halogen atoms and Y represents $C_1$-$C_3$ alkylene, as an effective ingredient, to the weeds.

7. A method for controlling the growth of undesirable weeds which comprises applying a herbicidally effective amount of a compound of the formula:

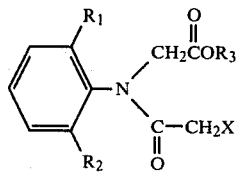

wherein $R_1$, $R_2$ and $R_3$ individually are methyl or ethyl and x is chlorine.

8. The method according to claim 1, wherein said effective ingredient is the compound of the formula:

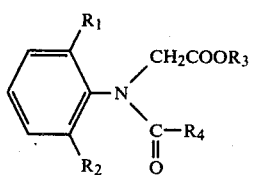

wherein $R_1$, $R_2$, $R_3$ and $R_4$ are the same as defined in claim 6.

9. The method according to claim 6, wherein said effective ingredient is the compound of the formula:

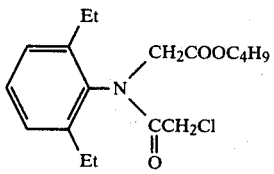

10. The method according to claim 6, wherein said effective ingredient is the compound of the formula:

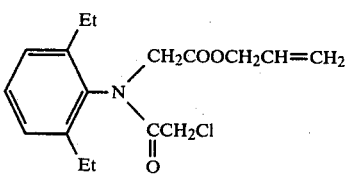

11. The method according to claim 6, wherein said effective ingredient is the compound of the formula:

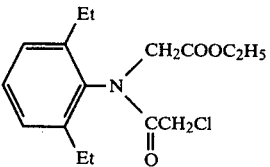

* * * * *